United States Patent [19]

Seki et al.

[11] Patent Number: 4,545,809
[45] Date of Patent: * Oct. 8, 1985

[54] HERBICIDAL N-(5-T-BUTYL-3-PYRAZOLYL) CARBAMATES

[75] Inventors: Nansho Seki; Yuki Yamaguchi; Yukihiro Nakamura; Hiroshi Kubo; Tetsuo Tsuruya, all of Tokyo, Japan

[73] Assignee: SDS Biotech K.K., Tokyo, Japan

[*] Notice: The portion of the term of this patent subsequent to Feb. 26, 2002 has been disclaimed.

[21] Appl. No.: 623,880

[22] Filed: Jun. 25, 1984

[30] Foreign Application Priority Data

Jun. 23, 1983 [JP] Japan ................... 58-111894

[51] Int. Cl.$^4$ ................. A01N 43/56; C07D 231/38; C07D 231/40
[52] U.S. Cl. ....................... 71/92; 548/375; 548/362
[58] Field of Search ............ 548/362, 375, 377; 71/92

[56] References Cited

U.S. PATENT DOCUMENTS

| 3,754,887 | 8/1973 | Brantley ................. | 548/362 |
| 3,920,690 | 11/1975 | Harrington ............. | 548/362 |
| 3,920,693 | 11/1975 | Ege ........................ | 548/362 |
| 4,146,632 | 3/1979 | Hofer et al. ............ | 548/362 |
| 4,260,775 | 4/1981 | Plath et al. ............ | 548/362 |

FOREIGN PATENT DOCUMENTS

| 55-89293 | 7/1980 | Japan ................. | 548/362 |
| 1598900 | 9/1981 | United Kingdom ...... | 548/362 |
| 2099420 | 12/1982 | United Kingdom ...... | 548/362 |

OTHER PUBLICATIONS

Dorn et al., Justus Liebigs Ann. Chem., 707, pp. 141-146 (1967).
Fomum et al., Tetrahedron Letters, No. 13, pp. 1101-1104 (1975).
Wagner and Zook, Synthetic Organic Chem., Wiley & Sons, pp. 646-647 (1953).

Primary Examiner—Richard A. Schwartz
Assistant Examiner—Kurt G. Briscoe
Attorney, Agent, or Firm—Sughrue, Mion, Zinn, Macpeak & Seas

[57] ABSTRACT

A pyrazole derivative represented by the formula (I):

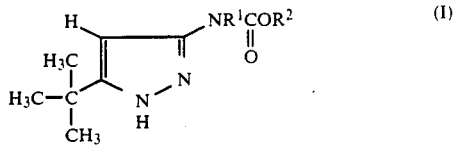

wherein $R^1$ and $R^2$ each represents a lower alkyl group, which has herbicidal activity, is disclosed. A process for preparing the pyrazole derivative of the formula (I) is also disclosed. A herbicide containing as an active ingredient the pyrazole derivative of the formula (I) is further disclosed as is a method for using the herbicide.

6 Claims, No Drawings

HERBICIDAL N-(5-T-BUTYL-3-PYRAZOLYL) CARBAMATES

FIELD OF THE INVENTION

The present invention relates to novel pyrazole derivative compounds and more particularly to alkyl N-alkyl-N-(5-t-butyl-3-pyrazolyl)carbamates and their method of preparation and use as herbicides.

SUMMARY OF THE INVENTION

This invention is comprised of novel pyrazole derivatives, in particular, alkyl N-alkyl-N-(5-t-butyl-3-pyrazolyl)carbamates represented by the formula (I):

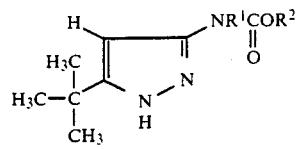

wherein $R^1$ and $R^2$ each represents a lower alkyl group, and a process for preparing the compound of the formula (I). This invention is further comprised of a herbicide containing the compound of the formula (I) as an active ingredient.

DETAILED DESCRIPTION OF THE INVENTION

With respect to the compound of the formula (I), there is a possible tautomer represented by the formula (I') as illustrated below.

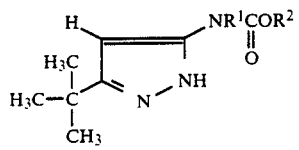

However, in the following explanation, this tautomer is representatively expressed by the formula (I).

In the formula (I), the lower alkyl group for $R^1$ and $R^2$ is preferably those having 1 to 4 carbon atoms and more preferably a methyl group.

The compound of the formula (I) is characterized by having a t-butyl group at the 5-position of the pyrazole ring thereof, such characteristic together with other characteristics having a great meaning in herbicidal activity.

The compound of the formula (I) exhibits strong herbicidal activity against a wide range of weeds, and if it is applied to the weeds in an amount of from 0.5 to 10 kg/ha before the emergence of the weeds or at the early growth stage thereof, it can control a wide range of the weeds within about 1 to 2 weeks.

In other words, when the application amount of the compound of this invention is controlled, or an appropriate application method is employed, it can selectively control various weeds which grow in cultivation fields for crops, such as corn, potato, sugar beet, peanut, soybeans, sunflower, barley, wheat, sorghum, sugarcane, cotton, fruits and the like.

Typical compounds according to this invention are shown in Table 1 below.

TABLE 1

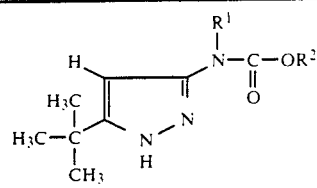

| Compound No. | $R^1$ | $R^2$ | NMR Analysis Data* H—NMR [δ value (ppm)] |
|---|---|---|---|
| 1 | $CH_3$ | $CH_3$ | 1.32 (s, 9H), 3.36 (s, 3H), 3.80 (s, 3H), 6.18 (s, 1H) |
| 2 | $CH_3$ | $C_2H_5$ | 1.32 (t, 3H), 1.32 (s, 9H), 3.37 (s, 3H), 4.25 (q, 2H), 6.18 (s, 1H) |
| 3 | $C_2H_5$ | $CH_3$ | 1.24 (t, 3H), 1.34 (s, 9H), 3.80 (s, 3H), 3.88 (q, 2H), 6.18 (s, 1H) |

*The NMR analysis was carried out in $CDCl_3$ at 60 MHz in which tetramethylsilane was used as an internal standard, and symbols of s, t and q represent singlet, triplet and quartet, respectively.

Of these, Compound No. 1 is particularly preferred since it exhibits strong herbicidal activity even in a small dosage.

The compound of the formula (I) can be prepared from 3-(N-alkylamino)-5-t-butylpyrazole (II) and a chloroformate (III), as follows:

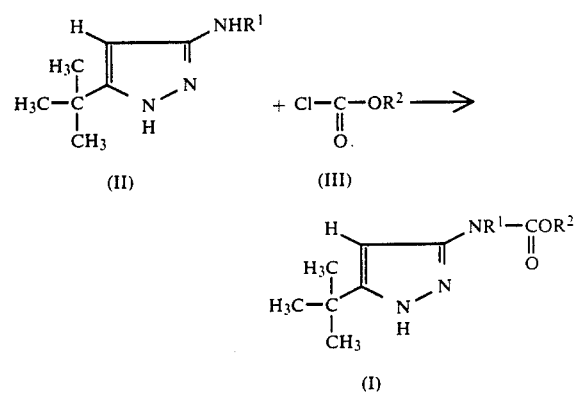

In the above reaction scheme, $R^1$ and $R^2$ are the same as defined above.

This reaction is preferably carried out by using water as the solvent and an inorganic base. In this case, the pH of the solution should be maintained around neutral so as to prevent decomposition of the chloroformate. For example, a chloroformate is added dropwise to the aqueous solution of the starting aminopyrazole and an inorganic base. The mixture is allowed to react, and a solid product is collected by filtration. Suitable examples of the inorganic base which can be used include alkali metal carbonates (e.g., sodium hydrogen carbonate, potassium hydrogen carbonate, sodium carbonate, potassium carbonate, etc.), alkali metal hydroxides (e.g., sodium hydroxide, potassium hydroxide, etc.), and the like.

A molar ratio of the chloroformate (III) to the aminopyrazole (II) is not restricted but in general can be used suitably in a range of from 1/1 to 1.5/1, preferably from 1/1 to 1.2/1. In this case, when the amount of the latter is too large, then unreacted products remain, whereas when the amount of the former is too large, then the NH moiety on the pyrazole ring more likely reacts. A molar ratio of the inorganic base to the chloroformate is preferably within the range of from 1/1 to 1.2/1. The reaction can be carried out at a temperature ranging from −10° C. to 40° C., preferably from 0° C. to 20° C. A suitable time of the reaction is in a range of from 0.5 to 10 hours, preferably 1 to 5 hours.

The compound of the formula (I) may also be prepared by adding chlorocarbonates in a solution of the aminopyrazole (II) in an organic solvent (e.g., benzene, toluene, xylene, carbon tetrachloride, methylene chloride, dioxane, acetonitrile, acetone, etc.) and heating the mixture at a temperature ranging from 30° C. to 120° C. with stirring, while this process is inferior to the former process with respect to the yield of the compound of the formula (I).

The method of isolation of the desired product varies with the kinds of starting materials and solvent. For example, it can be isolated by a method in which after completion of the reaction, water or a diluted alkaline solution is added to the reaction mixture, the mixture is shaken, and the organic layer is concentrated and subjected to crystallization from a solvent such as hexane, etc., or a method in which after completion of the reaction, the solvent is distilled off, and a diluted alkaline solution and a solvent such as hexane are added to the residue to form crystals.

The compound of the formula (I) which can be prepared by the respective reactions described above is, in general, sparingly soluble in water, but it is easily soluble in conventional organic solvents (except hexane, pentane or other petroleum-type solvents) and particularly soluble in alcohols and acetone.

The aminopyrazole of the formula (II) which can be used as the starting material can be prepared by the reduction of acylaminopyrazole as illustrated in the following reaction scheme.

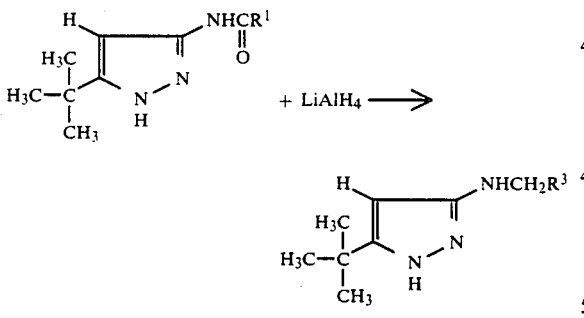

In the above reaction scheme, $R^3$ represents a hydrogen atom or a lower alkyl group, and the —$CH_2R^3$ group corresponds to $R^1$ in the formula (II).

The present invention is described in greater detail with reference to the following examples.

REFERENCE EXAMPLE

Preparation of 3-(N-Methylamino)-5-t-butylpyrazole (II)

21 g of lithium aluminum hydride was dissolved in 200 ml of tetrahydrofuran dried with metallic sodium, and 50 g of 3-formylamino-5-t-butylpyrazole was slowly added thereto, followed by heating the mixture with stirring under reflux conditions for 5 hours. After completion of the reaction, the reaction mixture was cooled, and 200 ml of ethyl acetate and 200 ml of water were dropwise added thereto. Then, insolubles were removed by filtration, and the ethyl acetate layer was washed with water and dried over anhydrous sodium sulfate, followed by distilling off the ethyl acetate. The resulting residue was allowed to stand for solidification whereby 45 g of 3-(N-methylamino)-5-t-butylpyrazole was obtained.

EXAMPLE 1

Preparation of Methyl N-(5-t-Butyl-3-pyrazolyl)-N-methylcarbamate (Compound No. 1)

15.5 g of 3-(N-methylamino)-5-t-butylpyrazole as prepared in Reference Example was dissolved in 50 ml of dioxane, and 11.3 g of methyl chloroformate was added to the solution. The mixture was then allowed to react at 100° C. for 5 hours. After the reaction was completed, the solvent was distilled off and the residue was dissolved in an alcohol. The solution was added in 200 ml of a 5% aqueous solution of sodium hydroxide and the mixture was stirred at room temperature for 30 minutes. After neutralization, the mixture was extracted with methylene chloride, and the methylene chloride layer was dried over anhydrous sodium sulfate, followed by distilling off the methylene chloride. The residue was recrystallized from a mixture of toluene and hexane, whereby 4 g of methyl N-(5-t-butyl-3-pyrazolyl)-N-methylcarbamate was obtained.

EXAMPLE 2

Preparation of Methyl N-(5-t-Butyl-3-pyrazolyl)-N-methylcarbamate 70 g of 3-(N-methylamino)-5-t-butylpyrazole as prepared in Reference Example was dissolved in 1.5 l of water together with 46 g of sodium bicarbonate, and 52 g of methyl chloroformate was added dropwise to the aqueous solution over 1.5 hours at 10° C. The mixture was allowed to react at 10° C. for 1 hour. After completion of the reaction, the solid product was collected by filtration, washed with water and hexane and dried to obtain 62 g of methyl N-(5-tert-butyl-3-pyrazolyl)-N-methylcarbamate.

The active compound according to this invention can be formulated into various formulations, e.g., emulsifiable concentrates, wettable powders, flowable formulations, dusts, granules, etc., by the application of a conventional manner for formulation.

Further, the compound of this invention can be mixed with other herbicides. Still further, in order to expand the scope of activity, the compound of this invention can be mixed with other pesticides than herbicides, such as plant growth regulators, insecticides, nematocides, fungicides, etc.

Typical formulations are explained by reference to the following Formulation Examples. In the Formulation Examples, all parts are by weight.

FORMULATION EXAMPLE 1

Preparation of Wettable Powder 50 parts of, as an active ingredient, each compound as shown in Table 1, 10 parts of diatomaceous earth, 35 parts of clay, 3 parts of sodium polyoxyethylene alkylaryl ether sulfonate and 2 parts of sodium alkylnaphthalenesulfonate were mixed and pulverized to obtain a wettable powder having 50% of the active ingredient.

In the use thereof, the wettable powder is diluted with water to a predetermined concentration and then subjected to spraying.

FORMULATION EXAMPLE 2

Preparation of Granule 5 parts of, as an active ingredient, each compound as shown in Table 1, 20 parts of bentonite, 73 parts of clay and 2 parts of sodium dodecylbenzenesulfonate were subjected to intimate mixing, and about 20 parts of water was added thereto. The resulting mixture was kneaded by means of a kneader, and passed through a granulator to form granules. The thus formed granules were dried and controlled in particle size to obtain granules having 5% of the active ingredient.

FORMULATION EXAMPLE 3

Preparation of Emulsifiable Concentrate 15 parts of, as an active ingredient, each compound as shown in Table 1, 80 parts of xylene and 5 parts of polyoxyethylene alkylaryl ether were mixed to form a homogeneous solution. Thus, an emulsifiable concentrate having 15% of the active ingredient was obtained.

In the use thereof, the emulsifiable concentrate is diluted with water to a predetermined concentration and then subjected to spraying.

The pyrazole derivative represented by the formula (I) has excellent herbicidal activity. Therefore, it is effective for controlling weeds growing in upland farms, orchards, non-cultivated fields, etc. When this active compound is applied on the surface of a soil or mixed with a soil, it can inhibit the growth of weeds and ultimately result in withering thereof. Further, it can control growing weeds by foliar application.

If the amount of the compound of this invention applied is chosen within a range of from 0.1 to 10 kg/ha, it can be used as a selective herbicide in cultivation fields for corn, wheat, barley, sugar beet, soybeans, peanut, sunflower, potato, cotton and fruits. Further, if the application amount is increased, the compound of this invention can be applied as a non-selective herbicide.

The compound of this invention can, for example, be used for controlling dicotyledons, e.g., velvetleaf (*Abtilon theophrasti*), pigweed (*Amaranthus retroflexus*), ragweed (*Ambrosia artemisiifolia*), aster (*Aster sublatus*), beggar-ticks (*Bidens pilosa*), moonflower (*Calonyction muricatum*), shepherdspurse (*Capsella bursa-pastoris*), sicklepod (*Cassis obtusifolia*), lambsquarters (*Chenopodium album*), field bindweed (*Convolvulus arvensis*), jimsonweed (*Datura stramonium*), bedstraw (*Galium aparine*), morning-glory (*Ipomea purpurea*), henbit (*Lamium amplexicaule*), pepperweed (*Lepidium virginicum*), woodsorrel (*Oxalis corniculata*), smartweed (*Polygonum nodosum*), purslane (*Portulaca oleracea*), buttercup (*Rananculus repens*), fieldcress (*Rorippa indica*), pearlwort (*Sagina japonica*), groundsel (*Senecio vulgaris*), coffee weed (*Sesbania exaltata*), prickly sida (*Sida spinosa*), nightshade (*Solanum nigrum*), spiny sowthistle (*Sonchus asper*), chickweed (*Stellaria media*), vetch (*vicia sativa*), cocklebur (*Xanthium pensylvanicum*), buckwheat (*Polygonum convulvulus*), etc.; monocotyledons, e.g., quackgrass (*Agropyron repens*), meadow foxtail (*Alopeculus pratensis*), wild oat (*Avena fatua*), crabgrass (*Digitaria sanguinalis*), barnyardgrass (*Echinochloa crus-galli*), goosegrass (*Eleusine indica*), Italian ryegrass (*lorium multiflorum*), fall panicum (*Panicum dichotomiflorum*), bluegrass (*Poa anua*), giant foxtail (*Setaria faberi*), green foxtail (*Setaria viridis*). Johnsongrass (*Sorghum halepens*), flatsedge (*Cyperus iria*), kyllinga (*Kyllinga brevifolia*), etc.

As described above, the compound of this invention has an excellent herbicidal activity against a wide range of weeds. The present invention can exhibit markedly high herbicidal activity when applied to the surface of a soil or to the foliar portions of weeds just before or after the germination of the weeds.

Further, when the compound of this invention is mixed with soil, it can also exhibit quite high herbicidal activity.

In order to explain the herbicidal activity of the compounds of the present invention, a series of Test Examples are shown.

TEST EXAMPLE 1

Pre-emergence Soil Treatment

Pots of 100 cm$^2$ were packed with volcanic ash soil and predetermined amounts of seeds of crabgrass (*Digitaria sanguinalis*), edible barnyardgrass (*Echinochloa crus-galli*), smartweed (*Polygonum nodosum*), pigweed (*Amaranthus retroflexus*), corn (*Zea mays*), wheat (*Triticum aestivum*) and mung bean (*Phaseolus radiatus*) were sown in each pot, followed by covering with soil to a depth of about 5 mm. On the same day, a wettable powder containing each compound as shown in Table 2 was diluted with water and applied to the surface of the soil in each pot in an amount of active ingredient of 10 kg/ha or 2.5 kg/ha. The herbicidal activity was visually evaluated two weeks after the application. The results obtained are shown in Table 2. Ratings of growth inhibition shown in Table 2 were given on a scale of 0-5 grades in which the grade 5 indicates a complete kill of the plant and the grade 0 no inhibition or substantially no inhibition.

5 = complete kill
4 = 80-99% damage
3 = 60-79% damage
2 = 40-59% damage
1 = 20-39% damage
0 = 0-19% damage

TABLE 2

| Compound | Dosage | Herbicidal Activity | | | | | | |
|---|---|---|---|---|---|---|---|---|
| No. | (kg/ha) | A | B | C | D | E | F | G |
| 1 | 10 | 5 | 5 | 5 | 5 | 4.5 | 5 | 5 |
|   | 2.5 | 5 | 5 | 5 | 5 | 4 | 5 | 5 |
| 2 | 10 | 5 | 3 | 5 | 5 | 0 | 4 | 5 |
|   | 2.5 | 1 | 1 | 3 | 4 | 0 | 0 | 0 |
| 3 | 10 | 5 | 5 | 5 | 5 | 2 | 5 | 5 |
|   | 2.5 | 5 | 5 | 5 | 5 | 0 | 5 | 5 |

A: Crabgrass (*Digitaria sanguinalis*)
B: Edible Barnyardgrass (*Echinochloa crus-galli*)
C: Smartweed (*Polygonum nodosum*)
D: Pigweed (*Amaranthus retroflexus*)
E: Corn (*Zea mays*)
F: Wheat (*Triticum aestivum*)
G: Mung Bean (*Phaseolus radiatus*)

TEST EXAMPLE 2

Foliar Spray (Post-emergence) Treatment

Ceramic pots of 100 cm$^2$ were packed with volcanic ash soil and predetermined amounts of seeds of crabgrass (*Digitaria sanguinalis*), edible barnyardgrass (*Echinochloa crus-galli*), smartweed (*Polygonum nodosum*), pigweed (*Amaranthus retroflexus*), corn (*Zea mays*), wheat (*Triticum aestivum*) and mung bean (*Phaseolus radiatus*) were sown, followed by covering with soil to a depth of about 1 cm. The resulting pots were allowed to stand in a greenhouse. When the respective plants grew up to a 1-2 leaf stage, a wettable powder containing each compound as shown in Table 3 was diluted with 1,000 l/ha of water and applied foliarly to the plants by means of a sprayer in an amount of active ingredient of 10 kg/ha or 2.5 kg/ha. Ten days after the application, the herbicidal activity was visually evaluated on the same scale as in Test Example 1. The results obtained are shown in Table 3.

TABLE 3

| Compound No. | Dosage (kg/ha) | Herbicidal Activity | | | | | | |
|---|---|---|---|---|---|---|---|---|
| | | A | B | C | D | E | F | G |
| 1 | 10 | 5 | 5 | 5 | 5 | 5 | 5 | 5 |
| | 2.5 | 5 | 5 | 5 | 5 | 4 | 5 | 5 |
| 2 | 10 | 4 | 2 | 5 | 5 | 1 | 2 | 4.5 |
| | 2.5 | 1 | 0 | 3 | 2 | 0 | 1 | 3 |
| 3 | 10 | 5 | 5 | 5 | 5 | 4 | 5 | 5 |
| | 2.5 | 4 | 0 | 5 | 5 | 0 | 1 | 4 |

A: Crabgrass (*Digitaria sanguinalis*)
B: Edible Barnyardgrass (*Echinochloa crus-galli*)
C: Smartweed (*Polygonum nodosum*)
D: Pigweed (*Amaranthus retroflexus*)
E: Corn (*Zea mays*)
F: Wheat (*Triticum aestivum*)
G: Mung Bean (*Phaseolus radiatus*)

TEST EXAMPLE 3

Foliar Spray (Post-emergence) Treatment

Ceramic pots of 325 cm² were packed with volcanic ash soil and predetermined amounts of seeds of corn (*Zea mays*), wheat (*Triticum aestivum*), soybean (*Glycine max*), sunflower (*Helianthus annus*), crabgrass (*Digitaria sanguinalis*), edible barnyardgrass (*Echinochloa crus-galli*), smartweed (*Polygonum nodosum*), prickly sida (*Sida spinosa*) and chickweed (*Stellaria media*) were sown, followed by covering with soil to a depth of about 1 cm. The resulting pots were allowed to stand in a greenhouse. When the respective plants grew up to a 1-2 leaf steage, a wettable powder containing each compound as shown in Table 4 was diluted with 1,000 l/ha of water and applied foliarly to the plants by means of a sprayer in an amount of active ingredient of 1 kg/ha, 2 kg/ha or 4 kg/ha. Twenty days after the application, the herbicidal activity was visually evaluated on the same scale as in Test Example 1. The results obtained are shown in Table 4.

TABLE 4

| Compound No. | Dosage (kg/ha) | Herbicidal Activity | | | | | | | | |
|---|---|---|---|---|---|---|---|---|---|---|
| | | A | B | C | D | E | F | G | H | I |
| 1 | 1 | 1 | 2 | 3 | 3 | 4 | 4 | 5 | 5 | 5 |
| | 2 | 3 | 3 | 4 | 4 | 4 | 4 | 5 | 5 | 5 |
| | 4 | 3 | 4 | 4 | 4 | 5 | 5 | 5 | 5 | 5 |
| 3 | 1 | 0 | 0 | 3 | 0 | 2 | 1 | 5 | 3 | 5 |
| | 2 | 1 | 2 | 3 | 1 | 2 | 2 | 5 | 4 | 5 |
| | 4 | 2 | 4 | 4 | 4 | 4 | 3 | 5 | 5 | 5 |

A: Corn (*Zea mays*)
B: Wheat (*Triticum aestivum*)
C: Soybean (*Glycine max*)
D: Sunflower (*Helianthus annus*)
E: Crabgrass (*Digitaria sanguinalis*)
F: Edible Barnyardgrass (*Echinochloa crus-galli*)
G: Smartweed (*Polygonum nodosum*)
H: Prickly Sida (*Sida spinosa*)
I: Chickweed (*Stellaria media*)

COMPARATIVE TEST EXAMPLE

Foliar Spray (Post-emergence) Treatment

Ceramic pots of 325 cm² were packed with volcanic ash soil and predetermined amounts of seeds of corn (*Zea mays*), wheat (*Triticum aestivum*), soybean (*Glycine max*), sunflower (*Helianthus annus*), tomato (*Lycopersicon esculentum*), carrot (*Daucus carota*), crabgrass (*Digitaria sanguinalis*), barnyardgrass (*Echinochloa crus-galli*), smartweed (*Polygonum nodosum*), prickly sida (*Sida spinosa*) and chickweed (*Stellaria media*) were sown, followed by covering with soil to a depth of about 1 cm. The resulting pots were allowed to stand in a greenhouse. When the respective plants grew up to various leaf stages as shown in Table 5, a wettable powder containing each compound as shown in Table 5 was diluted with 1,000 l/ha of water and applied foliarly to the plants by means of a sprayer in an amount of active ingredient of 0.5 kg/ha or 1 kg/ha. Twenty days after the application, the herbicidal activity was visually evaluated on the same scale as in Test Example 1. The results obtained are shown in Table 5.

TABLE 5

| | | Herbicidal Activity | | | |
|---|---|---|---|---|---|
| | | Methyl N—(5-t-butyl-3-pyrazolyl)-N—methylcarbamate (Compound No. 1) | | Methyl N—(5-t-butyl-3-pyrazolyl)carbamate (comparison) | |
| Plants | Leaf Stage | 0.5 kg/ha | 1 kg/ha | 0.5 kg/ha | 1 kg/ha |
| A | 4.0 l | 2 | 2.5 | 0 | 1 |
| B | 5.0 l | 2 | 2 | 1 | 1.5 |
| C | 1.5–2 l | 2.5 | 3.5 | 2 | 4 |
| D | 2.5 l | 1 | 4 | 1 | 1.5 |
| E | 1.5–2.0 l | 5 | 5 | 3.5 | 4 |
| F | 1.0 l | 0 | 1 | 0 | 1.5 |
| G | 2.5–3.0 l | 3 | 3.5 | 1 | 2.5 |
| H | 3.0–3.5 l | 3 | 3.5 | 0 | 1.5 |
| I | 2.0 l | 5 | 5 | 3.5 | 5 |
| J | 1.0–1.5 l | 1.5 | 5 | 0 | 3.5 |
| K | 3.0–6.0 l | 5 | 5 | 4.5 | 5 |

A: Corn (*Zea mays*)
B: Wheat (*Triticum aestivum*)
C: Soybean (*Glycine max*)
D: Sunflower (*Helianthus annus*)
E: Tomato (*Lycopersicon esculentum*)
F: Carrot (*Daucus carota*)
G: Crabgrass (*Digitaria sanguinalis*)
H: Barnyardgrass (*Echinochloa crus-galli*)
I: Smartweed (*Polygonum nodosum*)
J: Prickly Sida (*Sida spinosa*)
K: Chickweed (*Stellaria media*)

As is clear from Table 5 above, the N-alkylaminopyrazole according to this invention are effective as herbicides even in a small dosage as compared to the aminopyrazole having no alkyl substituent on the amino group.

While the invention has been described in detail and with reference to specific embodiments thereof, it will be apparent to one skilled in the art that various changes and modifications can be made therein without departing from the spirit and scope thereof.

What is claimed is:

1. A pyrazole derivative represented by the formula (I):

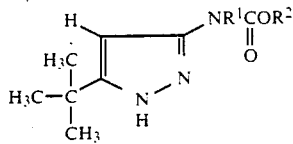

wherein R[1] and R[2] each represents an alkyl group having 1 to 4 carbon atoms.

2. Methyl N-(5-t-butyl-3-pyrazolyl)-N-methylcarbamate, as claimed in claim 1.

3. A herbicidal composition comprising as an active ingredient a herbicidally effective amount of a pyrazole derivative represented by the formula (I):

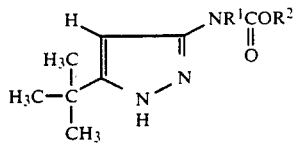

wherein R[1] and R[2] each represents an alkyl group having 1 to 4 carbon atoms and a carrier.

4. The herbicidal composition as claimed in claim 3, wherein the pyrazole derivative is methyl N-(5-t-butyl-3-pyrazolyl)-N-methylcarbamate.

5. A method for controlling noxious weeds comprising applying to plants or a locus, a herbicidally effective amount of a pyrazole derivative represented by the formula (I):

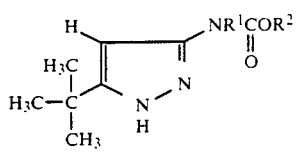

wherein R[1] and R[2] each represents an alkyl group having 1 to 4 carbon atoms.

6. The method as claimed in claim 5, wherein the pyrazole derivative is methyl N-(5-t-butyl-3-pyrazolyl)-N-methylcarbamate.

* * * * *